United States Patent [19]

Schwartz

[11] Patent Number: 4,906,633
[45] Date of Patent: Mar. 6, 1990

[54] PYRAZINE AMIDES

[75] Inventor: John A. Schwartz, Wilmington, Del.

[73] Assignee: ICI Americas Inc., Wilmington, Del.

[21] Appl. No.: 199,082

[22] Filed: May 26, 1988

[30] Foreign Application Priority Data

May 26, 1987 [GB] United Kingdom ............... 8712362
Mar. 2, 1988 [GB] United Kingdom ............... 8804984

[51] Int. Cl.$^4$ ................. A61K 31/495; C07D 241/20
[52] U.S. Cl. .................................. 514/255; 544/407
[58] Field of Search ..................... 544/407; 514/255

[56] References Cited

U.S. PATENT DOCUMENTS

| | | |
|---|---|---|
| 3,305,552 | 2/1967 | Cragoe, Jr. et al. |
| 3,544,568 | 12/1970 | Cragoe, Jr. et al. |
| 3,555,024 | 1/1971 | Cragoe, Jr. et al. ............... 544/407 |
| 3,567,725 | 3/1971 | Grabowski et al. ............... 544/407 |
| 3,577,418 | 5/1971 | Cragoe, Jr. et al. ............... 260/250 |
| 3,794,734 | 2/1974 | Cragoe et al. ..................... 424/330 |
| 3,809,721 | 5/1974 | Schultz et al. .................. 260/570.9 |
| 3,928,624 | 12/1975 | Cragoe, Jr. et al. |
| 4,029,816 | 6/1977 | Cragoe, Jr. et al. |
| 4,041,032 | 8/1977 | Murakami et al. ............... 544/407 |
| 4,085,211 | 4/1978 | Cragoe, Jr. et al. |
| 4,115,573 | 9/1978 | Cragoe, Jr. et al. ............... 544/407 |
| 4,272,537 | 6/1981 | Woltersdorf et al. ............. 544/207 |
| 4,399,138 | 8/1983 | Barlow et al. .................... 544/409 |
| 4,550,111 | 10/1985 | Barlow et al. .................... 544/407 |

FOREIGN PATENT DOCUMENTS

| | | |
|---|---|---|
| 57572 | 8/1982 | European Pat. Off. ............ 544/407 |
| 0086564 A1 | 1/1983 | European Pat. Off. |
| 86564 | 8/1983 | European Pat. Off. ............ 544/407 |
| 1181288 | 2/1970 | United Kingdom. |

OTHER PUBLICATIONS

Stokker, G. E., et al., *J. Med. Chem.*, 1980, 23, 1414–1427.
Edward J. Cragoe, Jr., *Diuretics Chemistry, Pharmacology, and Medicine*, (1983) 268–302: "2-Aminomethylphenols: A New Class of Saluretic Agent".
Cragoe, Jr., *Diuretics, Chemistry, Pharmacology, and Medicine*, pp. 268–302 (1983).

Primary Examiner—Mukund J. Shah
Assistant Examiner—Cecilia Shen
Attorney, Agent, or Firm—Rosemary M. Miano; Thomas E. Jackson; James T. Jones

[57] ABSTRACT

Novel pyrazine amides of Formula III (set out hereinafter) are disclosed which are useful as eukalemic diuretics.

7 Claims, No Drawings

PYRAZINE AMIDES

BACKGROUND OF THE INVENTION

This invention comprises novel pyrazine amides which are useful as eukalemic diuretics.

A variety of agents are available for use in treating hypertension. One particular class of such agents is diuretics. Diuretics are used for a variety of purposes, for example, reduction of fluid from the body and reduction of sodium levels in the body, for example, in the treatment of hypertension and edema. An example of a diuretic is 2-(aminomethyl)-4-(1,1-dimethylethyl)-6-iodophenol hydrochloride of formula I:

(Formula set out on pages following Examples) I discussed in U.S. Pat. No. 4,029,816 to Cragoe et al; and Stokker, G.E., J. Med. Chem., 1980, 23, 1414–1427. Additional diuretics include hydrochlorothiazide and chlorthalidone.

A problem with some diuretics is the reduction of serum potassium levels and complications caused from reductions of potassium beyond levels needed for maintaining physiological functions. Thus, some diuretics are used in conjunction with a potassium conserving agent such as 3,5-diamino-N-(aminoiminomethyl)-6-chloropyrazine carboxamide monohydrochloride, dihydrate of formula II:

(Formula set out on pages following Examples) II shown in U.S. Pat. No. 3,577,418 to Cragoe et al which is used in conjunction with, for example, thiazide diuretics.

There is thus a need for a single agent which is an effective but potassium-conserving (isokalemic, also called eukalemic) diuretic, such that it obviates the problems associated with hypokalemia (potassium depletion) and hyperkalemia (potassium buildup) without the need for taking multiple therapeutic agents.

A series of pyrazine-carboxamides has been described in U.S. Pat. No. 4,085,211 as eukalemic agents possessing diuretic and natriuretic properties. We have now discovered (and this is a basis for our invention) that, surprisingly, certain aminomethylphenol containing pyrazine amides of the formula III defined below possess eukalemic diuretic properties and are of value in treating those diseases and conditions in which a eukalemic diuretic effect is required, for example in treating edema, hypertension and/or related conditions.

SUMMARY OF THE INVENTION

The invention comprises compounds of formula III:
(Formula set out on pages following Examples) III
wherein:
R is hydrogen or methyl:
$R^4$ is selected from a group consisting of hydrogen and methyl;
A is chloro or bromo;
Z is selected from a group consisting of chloro, bromo and iodo:
and n is 1 or 2;
and pharmaceutically acceptable salts thereof.

Preferred values for the groups described above are:
for $R^4$: methyl;
for Z: bromo:
for A: chloro;
Preferred compounds are:
(a) 3,5-diamino-N-[2-[[2-[[2-[[[3-bromo-5-(1,1-dimethylethyl)-2-hydroxyphenyl]methyl]amino]ethyl]amino]-2-oxoethyl]methylamino]ethyl]-6-chloropyrazinecarboxamide; and
(b) 3,5-diamino-N-[2-[[3-[[2-[[[3-bromo-5-(1,1-dimethylethyl)-2-hydroxyphenyl]methyl]amino]ethyl]amino]-3-oxopropyl]methylamino]ethyl]-6-chloropyrazinecarboxamide.

It will be appreciated that certain of the compounds of formula III, for example those containing an asymmetrically substituted carbon atom, may exist in, and be isolated in, optically-active and racemic forms. Some compounds may exhibit polymorphism. It is to be understood that the present invention encompasses any racemic, optically-active, tautomeric, polymorphic or stereoisomeric form, or mixtures thereof, which form possesses the properties described above, it being well known in the art how to prepare optically-active forms (for example, by resolution of the racemic form or by synthesis from optically-active starting materials).

The compounds of the present invention may be prepared by methods which include those known in the art. For the methods described below "Pyz" has the meaning shown in formula V:
(Formula set out on pages following Examples) V
Halo or halogen is chloro, bromo or iodo. Such methods for preparation of a compound of formula III include the following:

(A) Reductively alkylating a selected pyrazinamidoamine of formula XI
(Formula set out on pages following Examples) XI
with an appropriate carbonyl compound of formula XII (i.e., a salicylaldehyde of formula XII for R=hydrogen or a ketone of formula XII for R=methyl):
(Formula set out on pages following Examples) XII
in a solvent such as ethanol or methanol, preferably, by in situ formation of an intermediate imine of formula XVII:
(Formula set out on pages following Examples) XVII
(which is formed but not isolated) and reduction with a reducing agent such as sodium borohydride or hydrogen and a catalyst. The desired reaction product is recovered by diluting the material with water to precipitate the product, which may be purified by crystallization from an appropriate solvent, such as methanol or ethanol.

(B) Alkylating a selected pyrazinamidoamine of formula XI:
(Formula set out on pages following Examples) XI
with an appropriate benzyl halide of formula XVIII:
(Formula set out on pages following Examples) XVIII and, preferably, in the presence of a base such as, for example, potassium carbonate or triethylamine, for example, for 1 to 5 days at, for example, room temperature. A solvent such as methanol or dimethylformamide is used. The desired reaction product is isolated by diluting the reaction mixture with water to precipitate the product, which may be purified by crystallization from an appropriate solvent, such as methanol or ethanol.

(C) Reacting a pyrazinamidoamine of formula XI with a phenol of formula XIX:
(Formula set out on pages following Examples) XIX and an aldehyde of formula RCHO, for example, under Mannich conditions, such as by heating at temperatures up to 100° for 1 to 5 days in an alcoholic or aqueous solution with an optional cosolvent such as tetrahydrofuran or dioxane. The desired reaction product is recovered by evaporation of the solvent and purified by crystallization from an alcohol such as ethanol.

(D) Reacting a particular pyrazinamido ester of formula IX:

(Formula set out on pages following Examples) IX wherein L is a (1-3C)alkyl group, such as, for example, methyl or ethyl, with a benzylic ethylenediamine of formula XX:

(Formula set out on pages following Examples) XX such as by heating them together at a temperature of up to 140° C. for, for example, 1 to 5 hours. The desired product may be purified by crystallization from an alcohol such as ethanol. The benzylic ethylenediamines of formula XX are prepared by mixing an aliphatic diamine with one of the amino groups suitably protected (for example, either as a phthalimide or butyloxycarbonyl (BOC) of formula XIII:

(Formula set out on pages following Examples) XIII where Q is a suitable protecting group such as BOC or phthalimide, with an appropriate carbonyl compound of formula XII in a solvent such as ethanol or methanol. The intermediate imines of formula XXI:

(Formula set out on pages following Examples) XXI are not isolated but stirred with a reducing agent such as sodium borohydride or hydrogen and a catalyst. The desired product is recovered by diluting the reaction mixture with water to precipitate the product, which may be purified by crystallization from a hydrocarbon solvent.

Removal of the protecting group provides the desired benzylic ethylenediamine of formula XX.

(E) For a compound of formula III wherein R is methyl, treating a corresponding intermediate imine of formula XVII wherein R is hydrogen with an organometallic agent such as, for example, methylmagnesium bromide, methylmagnesium chloride or methylmagnesium iodide. The desired product may be purified as described in Method (A).

An intermediate imine of formula XVII wherein R is hydrogen may be made by a conventional method, isolated by evaporation of the solvent, and redissolved in an appropriate inert solvent, such as, for example, ether or tetrahydrofuran, for reaction with an organometallic reagent.

(F) Halogenating a selected aminomethylphenolpyrazinamide (corresponding to a compound of formula III, but with Z=hydrogen) with a halogenating agent in a solvent such as acetic acid or methylene chloride. The desired product is recovered by evaporation of the solvent and crystallization from an appropriate solvent, such as methanol or ethanol.

(G) Dealkylating a selected aminomethylarylether-pyrazinamide of formula XXII:

(Formula set out on pages following Examples) XXII wherein $R^5$ is lower alkyl, such as, for example, methyl, with a dealkylating agent such as lithium thioethoxide or boron tribromide in a solvent such as dimethylformamide or methylene chloride respectively. The desired product is purified as described in method (A).

Intermediates of formula XI may be made as follows.

Pyrazinoic acids of formula $PyzCO_2H$ are prepared by the hydrolysis of the corresponding methyl esters of formula $PyzCO_2CH_3$. The hydrolysis is usually carried out using a solution of aqueous base such as sodium hydroxide and a solvent such as isopropanol or ethanol and stirring the mixture at room temperature for one to 24 hours. The pyrazinoicacid is then isolated by cooling and acidifying the mixture with an acid such as hydrochloric acid.

The pyrazinoyl imidazoles of formula VI:

(Formula set out on pages following Examples) VI are prepared by reacting the corresponding acids of formula $PyzCO_2H$ with 1,1-carbonyldiimidazole (slight excess) in a solvent such as dimethylformamide or methanol at room temperature and stirring the mixture for 10 to 24 hours. The pyrazinoyl imidazoles are isolated by dilution with methanol or water.

The pyrazinamides of formula VII:

(Formula set out on pages following Examples) VII are prepared by mixing the particular pyrazinoyl imidazole with an aliphatic diamine of formula VIII:

(Formula set out on pages following Examples) VIII and stirring at ambient temperature from 5 to 24 hours. A solvent such as tetrahydrofuran may be added or an excess of the diamine may be used as the solvent. The desired reaction product is recovered by evaporating the solvent to provide the product which can be purified by crystallization from an alcohol such as ethanol.

Pyrazinamido esters of formula IX:

(Formula set out on pages following Examples) IX are prepared by mixing the particular pyrazinamide of formula VII with an appropriate alkyl bromoester of formula X:

(Formula set out on pages following Examples) X (about 5-10% excess) where L is (1-3C)alkyl and a base such as potassium carbonate or triethylamine for 1 to 2 days at room temperature. A solvent such as methanol or dimethylformamide is used. The pyrazinamido ester is isolated by diluting it with water. It can be purified by recrystallization from an appropriate solvent such as ethanol. [*Note: When n=2 in formula X, an acrylic ester of formula Xa:

(Formula set out on pages following Examples) Xa may be substituted for the bromoester.]

Pyrazinamidoamines of formula XI:

(Formula set out on pages following Examples) XI are prepared by mixing the particular pyrazinamido ester with ethylenediamine of formula $H_2N\text{-}(CH_2)_2\text{-}NH_2$ (twofold excess) and heating at temperatures up to 100° C., preferably about 40° C., for 1 to 24 hours. A solvent such as an alcohol, for example, 2-propanol may be added or an excess of the amine may be used as the solvent. The desired reaction product is recovered by evaporation of the solvent and excess diamine.

Another method for the preparation of a pyrazinamidoamine of formula XI begins with an aliphatic diamine with one of the amino groups suitably protected (for example, either as a phthalimide or butyloxycarbonyl (BOC)). Such a compound is shown in formula XIII:

(Formula set out on pages following Examples) XIII where Q is a suitable protecting group such as BOC or phthalimide. Reaction of this monoprotected diamine with a haloalkanoyl halide of formula XIV:

(Formula set out on pages following Examples) XIV where Hal is chloro, bromo or iodo, in a solvent such as tetrahydrofuran or dioxane at ambient temperature in the presence of an acid scavenger such as triethylamine or potassium carbonate or N-methylmorpholine, provides the acylated diamine of formula XV:

(Formula set out on pages following Examples) XV which may be purified by distillation. Treatment of the acylated diamine with a suitable pyrazinamide of formula VII and a base such as triethylamine or potassium carbonate either neat or in a solvent such as tetrahydrofuran or dimethylformamide provides the appropriate protected pyrazinamidoamine. The protected pyrazinamidoamine of formula XVI:

(Formula set out on pages following Examples) XVI is isolated by diluting with water. It can be purified by crystallization from an appropriate solvent. Removal of the protecting group provides the desired pyrazinamidoamine of formula XI.

Pharmaceutically acceptable salts may be obtained using standard procedures well known in the art, for example, by reacting a compound of formula III with a suitable acid affording a physiologically acceptable anion, such as, for example, sulfuric acid, hydrochloric acid or citric acid.

As stated previously, the compounds of this invention or a salt thereof may be useful in the treatment of hypertension or edema and particularly as diuretics, especially eukalemic diuretics. The compounds of formula III are of value as pharmacological standards for the development and standardization of new disease models and assays for use in developing new therapeutic agents for treating hypertension.

When used in the treatment of one or more of the above mentioned diseases, a compound of formula III or a salt thereof may generally be administered as an appropriate pharmaceutical composition which comprises a compound of formula III as defined hereinbefore or a salt thereof together with a pharmaceutically acceptable diluent or carrier, the composition being adapted for the particular route of administration chosen. Such compositions are provided as a further feature of the invention. They may be obtained by employing conventional procedures and excipients and binders and may be in a variety of dosage forms. For example, they may be in the form of tablets, capsules, solutions or suspensions for oral administration: in the form of suppositories for rectal administration; in the form of sterile solutions or suspensions for administration by intravenous or intramuscular injection or infusion; and in the form of powders together with pharmaceutically acceptable inert solid diluents such as lactose.

For oral administration a tablet or capsule containing up to 250 mg (and typically 5 to 100 mg) of a compound of formula III or a salt thereof may conveniently be used. Similarly, for intravenous or intramuscular injection or infusion a sterile solution or suspension containing up to 10% w/w (and typically 0.05 to 5% w/w) of a compound of formula III or a salt thereof may conveniently be used.

The dose of compound of formula III or a salt thereof to be administered will necessarily be varied according to principles well known in the art taking account of the route of administration and the severity of the condition and the size and age of the patient under treatment. However, in general, a compound of formula III or a salt thereof will be administered to a warm-blooded animal (such as man) so that a dose in the range of, for example, 0.05 to 25 mg/kg (and usually 0.5 to 10 mg/kg) is received.

The diuretic and eukalemic properties of a compound of formula III may be demonstrated by using standard tests.

Test A:

Method. Female Beagle dogs are selected from an established breeding colony (weight range 9.0–13.0 kg), placed on a special diet of certified dog food and one can of Prescription Diet P/D Dog Food and observed for suitability for training. Dogs are selected from this group for training. Over a one to two week period the dogs are allowed to gradually build up tolerance to light restraint, standing, or sitting in a mesh sling support stand. Maximum time in sling is approximately 9 hours. Also, relaxed acceptance of the process of urinary bladder catheterization is accomplished during the training period. Sterile Bardex foley catheters (sizes 8, 10 pediatric) are used. The conscious female Beagle dogs with free access to water are fasted overnight. The dogs are placed in sling support stands (Alice King Chatham) and catheterized. A short equilibration period of about 30 minutes allows time for residual urine to be drained from the bladder. Urine spontaneously voided is collected in 50 ml pre-weighed tubes (Falcon). Two 1-hour control periods are followed by oral dosing with gelatin capsules containing test compounds or standard diuretics. Alternatively, some compounds are administered via oral gavage tubes in 10 ml quantities. No water loading is done. Spontaneously voided urine is collected for an additional six hours for a total collection period of eight hours. Afterward, dogs are returned to cages and fed and watered. Experiments are conducted once every two weeks on each dog, thus assuring adequate recovery between tests. Urine samples are weighed and measured for volume. Analysis of urinary electrolytes (sodium, potassium, chloride) is done on the following day. The analysis of urinary electrolytes showed results similar to other diuretics except that there was no excessive potassium loss.

Test B:

Method: Beagle dogs obtained from the established breeding colony of Marshall Animal Facility or White Eagle Laboratories are utilized. Healthy male and/or female Beagles 9–13 kg in body weight are housed according to standard operating procedure (SOP) for Veterinary Services and are placed on a diet of "certified" dry dog food supplemented with one can of puppy diet (P/D) prescription Diet dog food, with free access to water. A two-week minimum period of equilibration on this diet is necessary before determination of basal level electrolytes is attempted.

Prior to beginning actual drug dosing, six control blood samples are obtained to establish a range for basal level electrolytes. Control samples are evaluated for consistency in plasma $K^+$ levels, and a range of less than 0.25 mEq of $K^+$ is usually desirable. Historically, plasma $K^+$ levels in the range of 4.00–4.30 mEq have been obtained. Any dog not approximating these values is normally dropped from the study.

Sampling Procedure: Plasma samples are obtained by forearm venopuncture via the saphenous vein or the jugular vein. A 5 cc syringe with 20 gauge needle is used to obtain one 5 cc sample. The sample is preserved with 100 μl of 1000 unit heparin. Samples are centrifuged for ten minutes at 2500 rpm. Plasma is then pipetted into an appropriately labeled tube and all samples are frozen to await electrolytes determination.

Drug Dosing Schedule and Preparation: After control samples are analyzed, the dogs are divided randomly into groups, allowing a minimum of four dogs per drug group. Test compounds are dosed on a mg/kg basis. Gelatin capsules size "2 "00 and "3 "000 are used. Alternatively, some compounds are administered via oral gavage tubes. Compounds are suspended in 10 ml of saline by sonicating. The weight of the dog is determined by averaging the values over the three days of controls. Time of day for drug dosing is consistent throughout the study. Samples are required on days 4, 7, 11, 14, 21, and 28. Dosing takes place mid-morning (10 a.m. to 11 a.m.), and blood is drawn approximately three hours after dosing (1 p.m. to 2 p.m.). (Drug capsules are dosed orally followed by 5–10 milliliters of water from a syringe with oral dosing needle attached.) Hematocrits are taken with Microhematocrit capillary tubes and read immediately following collection of plasma samples.

Data Evaluation: Plasma samples are analyzed for potassium, as described above and showed no substantial change in serum potassium.

In general, the compounds of this invention which were tested showed a profile as eukalemic diuretics. Compounds of this invention which were tested have not shown any signs of overt toxicity following oral administration at a dose several multiples of the recommended therapeutic dose.

The invention will now be illustrated by the following non-limiting examples in which, unless stated otherwise:

(i) all operations were carried out at room or ambient temperature, that is, at a temperature in the range of 18°–25° C.;

(ii) evaporation of solvent was carried out using a rotary evaporator under reduced pressure (600–4000 pascals; 4.5–30 mm Hg) with a bath temperature of up to 60° C.:

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by thin layer chromatography (TLC) and reaction times are given for illustration only:

(v) melting points are uncorrected and (d) indicates decomposition: the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical date;

(vii) yields are given for illustration only:

(viii) when given, NMR data is in the form of delta values for major diagnostic protons, given in parts per million (ppm) relative to tetramethylsilane (TMS) as an internal standard, determined at 80 MHz or 250 MHz using $CDCl_3$ or DMSO-$d_6$ as solvent; conventional abbreviations for signal shape are used, for example: s, singlet: d, doublet; m, multiplet; br, broad; etc.; in addition "Ar" signifies an aromatic group or signal:

(ix) chemical symbols have their usual meanings; the following abbreviations have also been used: v (volume), w (weight); mp (melting point), [liter(s)], ml (milliliters), g [gram(s)], mg [milligram(s)];

(x) TLC solvent systems: Solvent System A: 25:5:70 (v/v/v) methanol:triethylamine:methylene chloride:

(xi) some compounds are denoted by letters, for example (A), for later reference in the Examples;

(xii) drying the organic phase was accomplished by swirling with sodium sulfate:

(xiii) solvent ratios are given in volume: volume (v/v) terms: and (xiv) for Examples 1–6, R is hydrogen.

EXAMPLE 1

3,5-Diamino-N-[2-[[2-[[2-[[[3-bromo-5-(1,1-dimethylethyl)-2-hydroxyphenyl]methyl]amino]ethyl]amino]-2-oxoethyl]methylamino]ethyl]-6-chloropyrazinecarboxamide amide (Formula III, A=Cl, $R^4$=$CH_3$, n=1, Z=Br).

(a) A solution of 1.72 g (5.2 mmol) of 3,5-diamino-N-[2-[[2-[(2-aminoethyl)amino]-2-oxoethyl]methylamino]ethyl]-6-chloropyrazinecarboxamide (A) and 1.2 g (5.0 mmol) of 2-hydroxy-3-bromo-5-(1,1-dimethylethyl)benzaldehyde (see L. C. Felton and J. H. Brewer, Science, 105:409 (1947) for a method of obtaining this material) in 30 ml of methanol was stirred at ambient temperature for 1 hour. Sodium borohydride (0.19 g, 5 mmol) was added and the reaction mixture stirred for 1 hour. The solvent was evaporated and the residue was partitioned between water and methylene chloride. The organic phase was dried ($Na_2SO_4$) and evaporated. The residue was chromatographed on 50 g of silica gel eluted with 4:96 (v/v) methanol: methylene chloride to give 1.78 g (3.0 mmol, 61%) of the title compound as a light yellow solid after trituration with hexane: mp 93°–95° C.

Analysis calculated for: $C_{23}H_{34}BrClN_8O_3$: C, 47.15; H, 5.85; N, 19.12; Found: C, 46.84; H, 5.75; N, 18.87

A sample of the title compound was converted into an oxalate salt in ethanol; mp 162°–163° C.

Analysis calculated for: $C_{23}H_{34}BrClN_8O_3 2C_2H_2O_4$: C, 42.34; H, 5.00: N, 14.63; Found: C, 42.36; H, 5.04: N, 14.45

The starting material (A) was obtained as follows.

(b) A mixture of 24.0 g (100.0 mmol) of 1-(3,5-diamino-6-chloropyrazinoyl)imidazole (see U.S. Pat. No. 4,029,816 as an example of how to obtain this material) and 13.61 g (183.5 mmol) of N-methylethylenediamine in 100 ml of tetrahydrofuran was stirred at ambient temperature for 18 hours. The reaction mixture was filtered and evaporated. The residue was crystallized from 2-propanol to give 20.8 g (85.0 mmol, 85%) of 3,5-diamino-6-chloro-N-(2-methylaminoethyl)pyrazine-2-carboxamide; mp 142.5°–143° C.

Analysis calculated for: $C_8H_{13}ClN_6O$: C, 39.27; H, 5.35; N, 34.35; Found: C, 39.28; H, 5.26; N, 34.55

(c) A mixture of 4.89 g (20.0 mmol) of 3,5-diamino-6-chloro-N-(2-methylaminoethyl)pyrazine-2-carboxamide, 3.1 g (20.0 mmol) of methyl bromoacetate and 2.0 g (20.0 mmol) of triethylamine was stirred in 30 ml of methanol at ambient temperature for 18 hours.

The solvent was stripped and the residue partitioned between saturated aqueous sodium bicarbonate solution and methylene chloride. The organic phase was dried and filtered through 50 g of silica gel eluted with methylene chloride. Evaporation of the solvent gave 6.2 g (19.6 mmol, 98%) of N-[2-[[(3,5-diamino-6-chloropyrazinyl)carbonyl]amino]ethyl]-N-methylglycine methyl ester as a light yellow solid; mp 132.5°–133.5° C.

Analysis calculated for $C_{11}H_{17}ClN_6O_3$: C, 41.71; H, 5.41: N, 26.53; Found: C, 41.88; H, 5.41; N, 26.51

(d) A solution of 2.3 g (7 26 mmol) of N-[2-[[(3,5-diamino-6-chloropyrazinyl)carbonyl]-amino]ethyl]-N-methyl glycine methyl ester in 0.9 g (15.0 mmol) of ethylene diamine was heated on a steam bath for 2 hours. The excess ethylene diamine was evaporated. The residue was triturated with 2-propanol. There was obtained 1.72 g (5.2 mmol, 72%) of 3,5-diamino-N-[2-[[(2-aminoethyl)amino]-2-oxoethyl]methylaminoethyl]-6-chloropyrazinecarboxamide as a light yellow solid; mp 106°-109° C; $R_f$=0.23, Solvent System A.

EXAMPLE 2

3,5-Diamino-N-[2-[[3-[[2-[[[3-bromo-5-(1,1-dimethylethyl)-2-hydroxyphenyl]methyl]amino]ethyl]amino]-3-oxopropyl]methylamino]ethyl]-6-chloropyrazinecarboxamide (Formula III, A=Cl, $R^4$=CH$_3$, n=2, Z=Br).

(a) A solution of 900 mg (2.5 mmol) of 3,5-diamino-N-[2-[[3-[(2-aminoethyl)amino]-3-oxopropyl[methylamino]ethyl]-6-chloropyrazinecarboxamide (B) and 650 mg (2.5 mmol) of 2-hydroxy-3-bromo-5-(1,1-dimethylethyl)benzaldehyde in 30 ml of methanol was stirred at ambient temperature for 1 hour. Sodium borohydride (0.10 g, 3.0 mmol) was added and the reaction mixture stirred for 1 hour. The solvent was evaporated and the residue was partitioned between water and methylene chloride. The organic phase was dried and evaporated. The residue was chromatographed on 25 g of silica gel eluted with 5:95 (v/v) methanol:methylene chloride. There was obtained 800 mg (1.33 mmol, 53%) of the title compound as a white solid after recrystallization from 2-propanol; mp 146.5°-147° C.

Analysis calculated for C$_{24}$H$_{36}$BrClN$_8$O$_3$: C, 48.05: H, 6.04; N, 18.68; Found: C, 48.00; H, 5.85; N, 18.67

A sample of the title compound was converted into an oxalate salt in ethanol, mp 118°-120° C.

Analysis calculated for
C$_{24}$H$_{36}$BrClN$_8$O$_3$2 C$_2$H$_2$O$_4$: C, 43.11; H, 5.17: N, 14.37; Found: C, 43.38; H, 5.21; N, 14.42

The starting material (B) was obtained as follows.

(b) A mixture of 24.0 g (100.0 mmol) of 1-(3,5-diamino-6-chloropyrazinoyl)imidazole and 13.6 g (183.5 mmol) of N-methylethylenediamine in 100 ml of THF was stirred at ambient temperature for 18 hours. The reaction mixture was filtered and evaporated. The residue was crystallized from 2-propanol to give 20.8 g (85.0 mmol, 85%) of 3,5-diamino-6-chloro-N-(2-methylaminoethyl)pyrazine-2-carboxide: mp 142.5°-143° C.

Analysis calculated for C$_8$H$_{13}$ClN$_6$O: C, 39.27; H, 5.35; N, 34.35;
Found: C, 39.28; H, 5.26; N, 34.55

(c) A mixture of 2.44 g (10.0 mmol) of 3,5-diamino-6-chloro-N-(2-methylaminoethyl)pyrazine-2-carboxamide, 1.67 g (10.0 mmol) of methyl 3-bromopropionate and 1.38 g (10.0 mmol) of potassium carbonate was stirred in 20 ml of DMF for 18 hours at ambient temperature. Water (100 ml) was added and the solid was filtered and air dried. Crystallization from ethanol provided 2.1 g (6.34 mmol, 63%) of N-[2-[[(3,5-diamino-6-chloropyrazinyl)carbonyl]amino]ethyl]-N-methyl-beta-alanine methyl ester as white crystals; mp 136.5°-137° C.

Analysis calculated for C$_{12}$H$_{19}$ClN$_6$O$_3$: C, 43.57; H, 5.79; N, 25.41. Found: C, 43.50: H, 5.76; N, 25.53

(d) A solution of 20.4 g (61.7 mmol) of N-[2-[[(3,5-diamino-6-chloropyrazinyl)carbonyl]amino]ethyl]-N-methyl-beta-alanine methyl ester and 36.0 g (0.6 mol) of ethylenediamine was heated at 40° C. for 2 days under an inert atmosphere. The excess ethylene diamine was evaporated. The residue was triturated with 2-propanol. There was obtained 15.2 g (44.4 mmol 72%) of 3,5-diamino-N-[2-[[3-[(2-aminoethyl)amino]-3-oxopropyl]-methylamino]ethyl]-6-chloropyrazinecarboxamide as a white solid; mp 140°-142° C.; $R_f$=0.27, Solvent System A.

Analysis calculated for C$_{13}$H$_{23}$ClN$_8$O$_2$: C, 43.51; H, 6.46; N, 31.23; Found: C, 43.23: H, 6.39; N, 30.92

EXAMPLE 3

The procedure described in Example 1 was repeated using a benzaldehyde of the formula XII where R=H, (see G. E. Stokker and E. M. Schultz, *Syn. Comm.*, 12:847 (1982) for a method of obtaining this material) to give a product of the formula IIIa:

(Formula set out on pages following Examples) IIIa wherein A is chloro and Z is iodo, as shown in Table I.

TABLE I

| Example | Z | Salt | mp (°C.) | % Yield |
|---|---|---|---|---|
| 3 | I | dioxalate | 162–164 | 68 |

EXAMPLES 4–5

The procedure described in Example 2 was repeated using benzaldehydes of the formula XII where R=H, to give products of the formula IIIb:

(Formula set out on pages following Examples) IIIb wherein A is chloro and Z has the values shown in Table II:

TABLE II

| Example | Z | Salt | mp (°C.) | % Yield |
|---|---|---|---|---|
| 4 | Cl | mono-HCl | 95–96 | 43 |
| 5 | I | di-HCl | 170–175 | 51 |

EXAMPLE 6

3,5-Diamino-N-[2-[[2-[[[3-bromo-5-(1,1-dimethylethyl)-2-hydroxyphenyl]methyl]amino]ethyl]amino]-2-oxoethyl]amino]ethyl]-6-chloropyrazinecarboxamide (Formula III, A=Cl, $R^4$=H, n=1, Z=Br).

(a) A solution of 4.07 g (12.3 mmol) of 3,5-diamino-N-[2-[[2-[(2-aminoethyl)amino]-2-oxoethyl]amino]ethyl]-6-chloropyrazinecarboxamide (K) and 3.16 g (12.3 mmol) of 2-hydroxy-3-bromo-5-(1,1-dimethylethyl)benzaldehyde in 150 ml of ethanol was stirred for 2 hours at ambient temperature. Sodium borohydride (0.56 g, 14.8 mmol) was added and the reaction mixture stirred for 20 minutes. The solvent was evaporated and the residue was partitioned between water and methylene chloride. The organic phase was dried and evaporated. The residue was chromatographed on silica gel (300 g) using a gradient from 0.2:5:94.8 to 0.2:10:89.8 (v/v/v) of ammonium hydroxide:methanol:methylene chloride as eluent. There was obtained 3.28 g (5.73 mmol, 47%) of the title compound as a white foam. This was converted into an oxalate salt in methanol; mp 203°-204° C.

Analysis calculated for C$_{22}$H$_{32}$BrClN$_8$O$_3$.2C, 41.52: H, 4.83; N, 14.90; Found: C, 41.83; H, 4.87; N, 15.23

The starting material (K) was obtained as follows:

(b) A mixture of 2.0 g (10.0 mmol) of methyl 3,5-diamino-6-chloropyrazine-2-carboxylate and 13.5 g (22.6 mmol) of ethylene diamine was allowed to stand for 3 days at ambient temperature. The excess amine was evaporated and the residue was crystallized from ethanol. There was obtained 1.38 g (5.9 mmol, 59%) of 3,5-diamino-6-chloro-N-(2-aminoethyl)pyrazine-2-carboxamide: mp 173°-174° C.

Analysis calculated for $C_7H_{11}ClN_6O$: C, 36.45: N, 4.81; N, 36.44; Found: C, 36.50; N, 4.71; N, 36.22

(c) A mixture of 13.7 g (59.4 mmol) of 3,5-diamino-6-chloro-N-(2-aminoethyl)pyrazine-2-carboxamide, 3.03 g (19.8 mmol) of methyl bromoacetate and 2.0 g (19.8 mmol) of triethylamine was stirred overnight in 250 ml of tetrahydrofuran at ambient temperature. The solvent was evaporated and the residue was chromatographed on silica gel (300 g) using 3.5:96.5 (v/v) methanol:-methylene chloride as eluent. There was obtained 4.45 g (14.7 mmol, 74%) of N-[2-[[(3,5-diamino-6-chloropyrazinyl)carbonyl]amino]ethyl]glycine methyl ester as a white powder; mp 145°–146.5° C.

Analysis calculated for $C_{10}H_{15}ClN_6O_3$: C, 39.67; H, 4.99; N, 27.76; Found: C, 39.66; H, 4.95: N, 27.65

(d) A solution of 7.45 g (24.6 mmol) of N-[2-[[(3,5-diamino-6-chloropyrazinyl)carbonyl]amino]ethyl]glycine methyl ester and 22.48 ml (373.9 mmol) of ethylenediamine was stirred at ambient temperature for two days. The excess diamine was evaporated. There was obtained 8.14 g (24.6 mmol, 100%) of 3,5-diamino-N-[2-[[2-[(2-aminoethyl)amino]2-oxoethyl]amino]ethyl]-6-chloropyrazinecarboxamide as a yellow solid: Rf=0.28, Solvent System A.

EXAMPLE 7

(±)-3,5-diamino-N-[2-[[3-[[2-[[1-[3-bromo-5-(1,1-dimethylethyl)-2-hydroxyphenyl]ethyl]amino]ethyl]amino]-3-oxopropyl]methylamino]ethyl]-6-chloropyrazinecarboxamide (Formula III, A=Cl, $R=R^4=CH_3$, Z=Br).

(a) A solution of 8.11 g (22.63 mmol) of 3,5-diamino-N-[2-[[3-[(2-aminoethyl)amino]-3-oxopropyl]methylamino]ethyl]-6-chloropyrazinecarboxamide (B) and 7.50 g (29.17 mmol) of 1-[3-bromo-5-(1,1-dimethylethyl)-2-hydroxyphenyl]ethanone (L) in 100 ml of methanol and 50 ml of methylene chloride was stirred for 1.5 hours at ambient temperature. Sodium borohydride (1.26 g, 33.31 mmol) was added and the reaction mixture stirred for 1 hour. The solvent was evaporated and the residue chromatographed on silica gel (250 g) using 3:97 (v/v) methanol:methylene chloride as eluent. There was obtained 9.11 g (14.83 mmol, 66%) of the title compound after trituration with ether; mp 100°–102° C.

Analysis calculated for $C_{25}H_{38}BrClN_8O_3$: C, 48.91: H, 6.24; N, 18.25; Found: C, 49.10: H, 6.06; N, 17.99

The starting material (L) was obtained as follows:

(b) A mixture of 12.86 g (50.0 mmol) of 2-hydroxy-3-bromo-5-(1,1-dimethylethyl)benzaldehyde and 3.82 g (55.0 mmol) of hydroxylamine hydrochloride in 30 ml of ethanol, 30 ml of water and 30 ml of tetrahydrofuran was cooled in an ice-water bath. Sodium bicarbonate (5.04 g, 60.0 mmol) was added in small portions over 15 minutes. After stirring for 1 hour at ambient temperature, water (200 mmol) was added and the solid was filtered and dried. There was obtained 13.2 g (48.5 mmol, 97%) of 2-hydroxy-3-bromo-5-(1,1-dimethylethyl)benzaldehyde oxime as a white solid; mp 167°–169° C.

Analysis for $C_{11}H_{14}BrNO_2$ Calculated: C, 48.55; H, 5.19; N, 5.15; Found: C, 48.33; H, 5.14; N, 4.93

(c) A mixture of 12.0 g (44.0 mmol) of 2-hydroxy-3-bromo-5-(1,1-dimethylethyl)benzaldehyde oxime and 18.9 g (90.0 mmol) of trifluoroacetic anhydride in 100 ml of tetrahydrofuran was cooled in an ice-water bath. A solution of 15.2 g (150.0 mmol) of triethylamine in 40 ml of tetrahydrofuran was added. After refluxing overnight, the solvent was stripped. The residue was partitioned between water and methylene chloride. The organic phase was washed with 1N hydrochloric acid followed by saturated sodium bicarbonate, then dried and evaporated. The residue was crystallized from hexane to provide 10.4 g (41.2 mmol, 94%) of 2-hydroxy-3-bromo-5-(1,1-dimethylethyl)-benzonitrile; mp 69°–71° C.

Analysis calculated for $C_{11}H_{12}BrNO$: C, 51.99; H, 4.76; N, 5.51; Found: C, 51.87: H, 4.77; N, 5.27

(d) To a solution of 10.4 g (41.2 mmol) of 2-hydroxy-3-bromo-5-(1,1-dimethylethyl)benzonitrile in 50 ml of tetrahydrofuran was added 47 ml (133.9 mmol, 2.85M) methylmagnesium bromide in ether. After stirring overnight at ambient temperature, the reaction mixture was poured onto ice and made acidic with 2N hydrochloric acid. The aqueous solution was extracted with ether. The organic phase was dried and evaporated. Crystallization from 2-propanol gave 10.5 g (38.7 mmol, 94%) of 1-[3-bromo-5(1,1-dimethylethyl)-2-hydroxyphenyl]ethanone: mp 98°–98.5° C.

Analysis calculated for $C_{12}H_{15}BrO_2$: C, 53.16; H, 5.58; Found: C, 53.19; H, 5.54

EXAMPLE 8

Capsule:
Each capsule contains:

| Material | Quantity/ 350 mg Blend |
|---|---|
| Compound of Example 2 | 120.0 mg. |
| Lactose, National Formulary (NF) Fast Flo | 175.0 mg. |
| Sodium starch glycolate, NF | 18.0 mg. |
| Pregelatinized starch, NF | 35.0 mg. |
| Magnesium stearate, NF | 2.0 mg. |

All of the above-listed materials, except the magnesium stearate, are screened through a suitable screen, for example, 20 mesh, and blended in a mixer for about 5 minutes. The magnesium stearate is then screened through a suitable screen, for example, 40 mesh, and the screened magnesium stearate is then added to the blended materials and mixed for 2 minutes. The blended powder is placed in a suitable and properly labeled container and encapsulated in two-piece hard gelatin capsules (size #0) as required.

EXAMPLE 9

Capsule:
Each capsule contains:

| Material | Quantity/ 350 mg Blend |
|---|---|
| Compound of Example 2 | 120.0 mg. |
| Lactose, National Formulary (NF) Fast Flo | 175.0 mg. |
| Microcrystalline cellulose | 18.0 mg. |
| Pregelatinized starch, NF | 35.0 mg. |
| Magnesium stearate, NF | 2.0 mg. |

All of the above-listed materials, except the magnesium stearate, are screened through a suitable screen, for example, 20 mesh, and blended in a mixer for about 5 minutes. The magesium stearate is then screened through a suitable screen, for example, 40 mesh, and the screened magnesium stearate is then added to the blended materials and mixed for 2 minutes. The blended powder is placed in a suitable and properly labeled container and encapsulated in two-piece hard gelatin capsules (size #0) as required.
FORMULAE
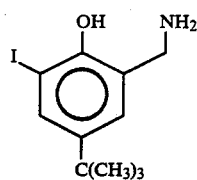 I
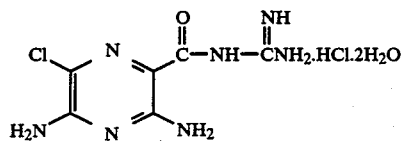 II
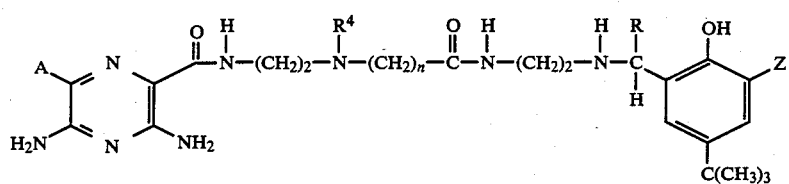 III
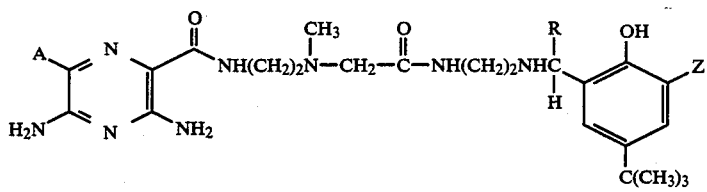 IIIa
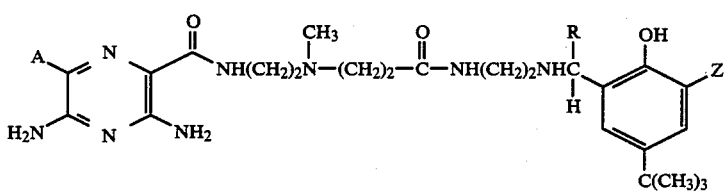 IIIb
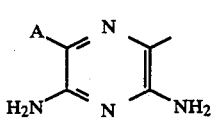 V
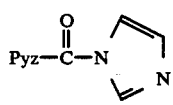 VI
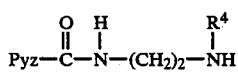 VII
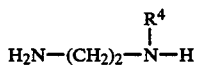 VIII
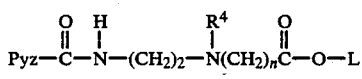 IX
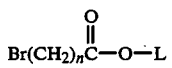 X
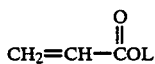 Xa -continued
FORMULAE
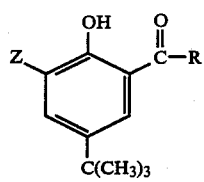 XI
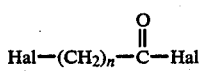 XII
H₂N—(CH₂)₂—NH—Q  XIII
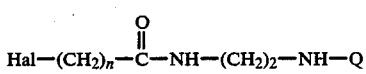 XIV
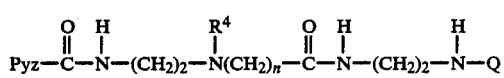 XV
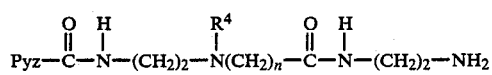 XVI
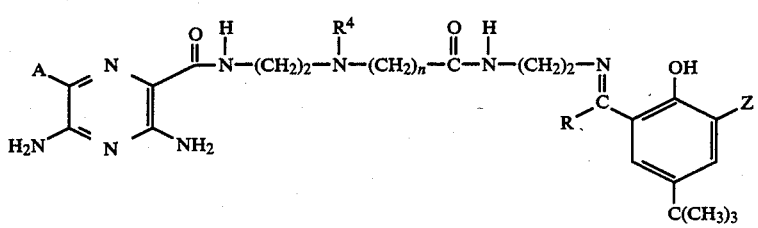 XVII
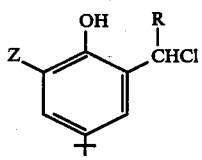 XVIII
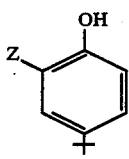 XIX
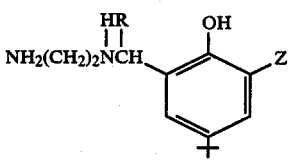 XX
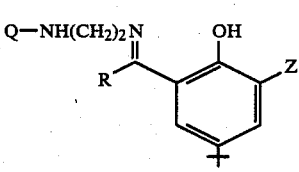 XXI FORMULAE
-continued

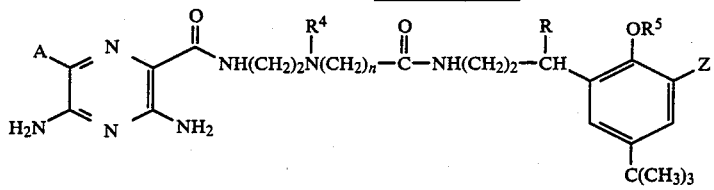

What is claimed is:
1. A compound having the formula

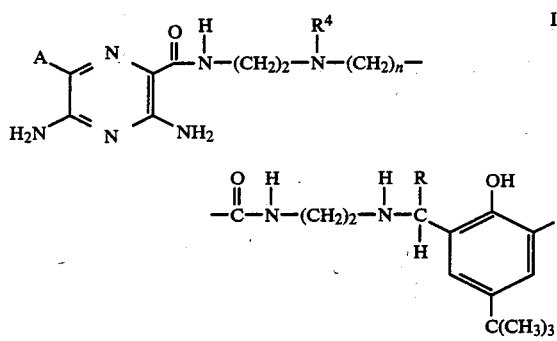

wherein:
R is hydrogen or methyl;
R⁴ is selected from a group consisting of hydrogen and methyl;
A is chloro or bromo;
Z is selected from a group consisting of chloro, bromo and iodo; and n is 1 or 2;
and pharmaceutically acceptable salts thereof.

2. A compound as claimed in claim 1 wherein $R^4$ is methyl Z is bromo; and A is chloro.
3. A compound as claimed in claim 1 selected from
  (a) 3,5-diamino-N-[2-[[2-[[2-[[[3-bromo-5-(1,1-dimethylethyl)-2-hydroxyphenyl]methyl]amino]ethyl]amino-2-oxoethyl]methylamino]ethyl]-6-chloropyrazinecarboxamide; and
  (b) 3,5-diamino-N-[2-[[3-[[2-[[[3-bromo-5-(1,1-dimethylethyl)-2-hydroxyphenyl]methyl]amino]ethyl]amino ]-3-oxopropyl]methylamino]ethyl]-6-chloropyrazinecarboxamide,
and pharmaceutically acceptable salts thereof.
4. A salt as claimed in claim 1 wherein said salt is an acid addition salt of an acid affording a physiologically acceptable anion.
5. A pharmaceutical composition useful as a eukalemic diuretic comprising a eukalemic diuretic amount of a compound of claim 1 or a pharmaceutically acceptable salt thereof and a non-toxic pharmaceutically acceptable diluent or carrier.
6. A method of inducing eukalemic diuresis in a mammal comprising administering to the mammal a pharmaceutically effective amount of a compound of claim 1.
7. A method of treating hypertension in a mammal comprising administering a pharmaceutically effective amount of a compound of claim 1 to a mammal in need of such treatment.

* * * * *